United States Patent [19]

Tsou et al.

[11] Patent Number: 4,552,705

[45] Date of Patent: Nov. 12, 1985

[54] METHOD OF MAKING TRI-(β-CYANOETHYL)AMINE

[75] Inventors: Dean T. Tsou, Solon; Sandra L. Denman, Brunswick Hills; James D. Burrington, Richmond Heights; Mark C. Cesa, South Euclid, all of Ohio

[73] Assignee: The Standard Oil Company, Cleveland, Ohio

[21] Appl. No.: 670,181

[22] Filed: Nov. 13, 1984

[51] Int. Cl.[4] ............................................. C07C 121/43
[52] U.S. Cl. ................................................. 260/465.5 R
[58] Field of Search .................................. 260/465.5 R

[56] References Cited

U.S. PATENT DOCUMENTS

| | | | |
|---|---|---|---|
| 2,448,013 | 8/1948 | Buc et al. ..................... | 260/465.5 R |
| 2,816,129 | 12/1957 | Montgomery ............... | 260/465.5 R |
| 3,770,798 | 11/1973 | Norton ......................... | 260/465.5 R |
| 4,271,088 | 6/1981 | Butte, Jr. et al. ........ | 260/465.5 R X |
| 4,271,089 | 6/1981 | Butte, Jr. et al. ........ | 260/465.5 R X |

OTHER PUBLICATIONS

Smolin et al., Ind. & Eng. Chem., 50, (1958), pp. 1115–1118.
Wiedeman et al., J.A.C.S., 67, (1945), pp. 1994–1996.
Whitmore et al., J.A.C.S., 66, (1944), pp. 725–731.

*Primary Examiner*—Joseph P. Brust
*Attorney, Agent, or Firm*—Charles S. Lynch; John E. Miller, Jr.; Larry W. Evans

[57] ABSTRACT

Disclosed is the liquid phase reaction of the acrylonitrile with ammonia in the presence of a large amount of a polar solvent having a high dielectric constant.

13 Claims, No Drawings

METHOD OF MAKING TRI-(β-CYANOETHYL)AMINE

This invention relates to a process for making tri-(β-cyanoethyl)amine by reaction of acrylonitrile and ammonia.

Tri-(β-cyanoethyl)amine has several known uses, for instance, as an additive in plasticized poly(vinyl acetate) coatings to increase tensile strength (see U.S. Pat. No. 3,316,197), and as a promoter in catalytic oxidation of alkylaromatic hydrocarbons to aromatic carboxylic acids (see German Application No. 2,258,503, June 17, 1973). In addition, this compound can be hydrolyzed to nitrilotripropionic acid which is useful as a boiler scale inhibitor and remover (see South African Pat. No. 6,802,227, Sept. 9, 1968 to Nalco Chemical Co.)

It is thus an object of the invention to provide a new and advantageous process for making tri-(β-cyanoethyl)amine.

Other objects, as well as features, aspects and advantages, of the invention will become apparent from a study of the present specification, including the examples and the claims.

According to the present invention, there is provided a process which comprises reacting ammonia and acrylonitrile in the liquid phase by mixing said reactants and a solvent and heating the reaction mixture in a reaction zone to a temperature in the range from 15° to 250° C., more usually from 60° to 160° C., in which the charge to the reaction zone contains from 2.5 to 30 moles of acrylonitrile per mole of ammonia, usually 3 to 12 moles, and from 20 to 300 moles of solvent per mole of ammonia, usually 50 to 150 moles, more usually 50 to 120 moles per mole of ammonia, thereby producing tri-(β-cyanoethyl)amine, said solvent being a highly polar solvent having a high dielectric constant usually selected from dimethylformamide, dimethyl sulfoxide, formamide, N-methylformamide, 1,2,3-propanetriol, N-methylpropionamide, diethylene glycol, hexamethylphosphoramide, triethanolamine and water. Other highly polar solvents having a high dielectric constant can also be employed.

Of course, at temperatures above atmospheric reflux temperature of the system the reaction must be effected in a closed reaction zone under at least autogenous pressure in order to maintain liquid phase reaction conditions.

The reaction is usually carried out for 1 to 20 hours depending on temperature, although longer and shorter times can be used.

The reaction of the present process can be represented by the equation $$3CH_2=CHCN + NH_3 \rightarrow N(CH_2CH_2CN)_3$$

The central and surprising novelty of the present invention is the discovery that large amounts of a high polar, highly dielectric constant solvent very significantly increase the selectivity of conversion of ammonia to tri-(β-cyanoethyl)amine.

The following examples of the invention are merely illustrative and are not to be considered in any way limiting.

EXAMPLES 1–7

In the following specific examples a mixture of the reactants acrylonitrile and ammonia together with water was heated in the molar ratios shown in Table 1 at the temperatures indicated. The reactions were all about 17–18 hours long. After the reaction mixture was cooled to room temperature, the organic products were extracted therefrom by $CDCl_3$ as solvent and analyzed by $^{13}C$ NMR. In the table the $NH_3$ conversion and the selectivity to di-(β-cyanoethyl)amine (DCA) and to tri-(β-cyanoethyl)amine (TCA) are shown. In examples 5–7 the reaction mixture was refluxed and the 80° C. shown in Table 1 is the approximate reflux temperature.

The prior art known to exist relative to the reaction of aqueous ammonia and water was directed toward making di-(β-cyanoethyl)amine, and thus did not employ ratios of acrylonitrile to ammonia even as high as 2:1. Thus, in Weidman and Montgomery, JACS,67 1994(1945) the molar ratio of acrylonitrile was less than 2:1 and very little TCA was made. It was thought that more TCA might be made if the acrylonitrile to $NH_3$ ratio were increased. This was done in comparative examples 1 and 5 with no effect.

TABLE 1

| Example No. | $AN/NH_3/H_2O$ mole ratio | Temp °C. | Percent $NH_3$ Conv. | Selectivity[a] to DCA | TCA |
|---|---|---|---|---|---|
| Comp. 1 | 10/1/2 | 27 | — | [b] | |
| 2 | 10/1/54 | 27 | — | 95 | 5 |
| 3 | 3/1/156 | 27 | — | 87 | 13 |
| 4 | 5/1/100 | 27 | — | 33 | 67 |
| Comp. 5 | 5/1/2 | 80 | 23.4 | 100 | 0 |
| 6 | 5/1/80 | 80 | 84 | 12 | 88 |
| 7 | 5/1/100 | 80 | 55 | 9 | 91 |

[a] No primary amine was formed.
[b] Only di-(β-cyanoethyl)amine was formed, with no mono-or-tri-(β-cyanoethyl)amine being formed.

Thus according to the surprising discovery of the present invention the key to increased conversion of the ammonia to TCA lies in the use of the very large amounts or ratio of water to $NH_3$, as set forth in the present claims.

As will be evident to those skilled in the art, modifications of this invention can be made or followed in the light of the foregoing disclosure without departing from the spirit and scope of the disclosure or from the scope of the claims.

What is claimed is:

1. A process which comprises reacting acrylonitrile with ammonia in the liquid phase at a temperature in the range from 15° to 250° C. in which process the reactants and a solvent are added to the reaction zone in the ratios of from 2.5 to 30 moles of acrylonitrile and from 20 to 300 moles of said solvent, per mole of ammonia, thereby producing tri-(β-cyanoethyl)amine, said solvent being a highly polar solvent having a high dielectric constant selected from dimethylformamide, dimethyl sulfoxide, formamide, N-methylformamide, 1,2,3-propanetriol, N-methylpropionamide, diethylene glycol, hexamethylphosphoramide, triethanolamine and water.

2. A process of claim 1 wherein the reaction temperature is in the range from 50° to 200° C.

3. A process of claim 1 wherein the reaction temperature is in the range from 60° to 160° C.

4. A process which comprises reacting acrylonitrile with ammonia in the liquid phase in the presence of water at a temperature in the range from 15° to 250° C. in which process the reactants and water are added to the reaction zone in the ratios of from 2.5 to 30 moles of acrylonitrile and from 20 to 300 moles of water, per mole of ammonia, thereby producing tri-($\beta$-cyanoethyl)amine.

5. A process of claim 4 wherein the reaction temperature is in the range from 15° to 200° C.

6. A process of claim 4 wherein the reaction temperature is in the range from 60° to 160° C.

7. A process of claim 4 wherein the water is added to the reaction zone in the amount of 50 to 150 moles per mole of ammonia.

8. A process of claim 5 wherein the water is added to the reaction zone in the amount of 50 to 150 moles per mole of ammonia.

9. A process of claim 6 wherein the water is added to the reaction zone in the amount of 50 to 150 moles per mole of ammonia.

10. A process of claim 4 wherein the water is added to the reaction zone in the amount of 50 to 120 moles per mole of ammonia.

11. A process of claim 5 wherein the water is added to the reaction zone in the amount of 50 to 120 moles per mole of ammonia.

12. A process of claim 6 wherein the water is added to the reaction zone in the amount of 50 to 120 moles per mole of ammonia.

13. A process of claim 6 wherein the water is added to the reaction zone in the amount of 50 to 120 moles per mole of ammonia and acrylonitrile is added to the reaction zone in the amount of 3 to 12 moles per mole of ammonia.

* * * * *